(12) United States Patent
Weiner et al.

(10) Patent No.: US 10,320,878 B2
(45) Date of Patent: Jun. 11, 2019

(54) SYSTEM AND METHOD FOR PRESERVING CAUSALITY OF AUDITS

(71) Applicant: Medidata Solutions, Inc., New York, NY (US)

(72) Inventors: Aaron Weiner, Brooklyn, NY (US); Matthew Szenher, New York, NY (US); Nolan Carroll, New York, NY (US); Isaac Wong, New York, NY (US)

(73) Assignee: Medidata Solutions, Inc., New York, NY (US)

( * ) Notice: Subject to any disclaimer, the term of this patent is extended or adjusted under 35 U.S.C. 154(b) by 1042 days.

(21) Appl. No.: 14/731,123

(22) Filed: Jun. 4, 2015

(65) Prior Publication Data
US 2015/0269326 A1    Sep. 24, 2015

Related U.S. Application Data (63) Continuation-in-part of application No. 14/053,405, filed on Oct. 14, 2013, now abandoned.

(51) Int. Cl.
*G06F 19/00* (2018.01)
*H04L 29/08* (2006.01)
(Continued)

(52) U.S. Cl.
CPC ............ *H04L 67/02* (2013.01); *G06F 16/273* (2019.01); *G06F 19/00* (2013.01);
(Continued)

(58) Field of Classification Search
None
See application file for complete search history.

(56) References Cited

U.S. PATENT DOCUMENTS

| | | | |
|---|---|---|---|
| 2003/0163488 A1* | 8/2003 | Kloos | G06F 19/326 |
| 2003/0208378 A1* | 11/2003 | Thangaraj | G06F 19/321 705/2 |

(Continued)

OTHER PUBLICATIONS

The International Search Report and Written Opinion of the International Searching Authority, PCT/US2014/060428, dated Jan. 21, 2015.

(Continued)

*Primary Examiner* — Michael Tomaszewski
(74) *Attorney, Agent, or Firm* — Steptoe & Johnson LLP; Robert Greenfield (57) ABSTRACT

A system for preserving causality of audits may include an upstream service, a downstream service, and an audit service. The upstream service receives a first request including a trace ID and a first span ID, generates a first audit concerning a resource owned by the upstream service and having the trace ID and the first span ID as metadata, persists the first audit to a first database, and generates a second request including the trace ID, a parent span ID, and a second span ID. The downstream service receives the second request from the upstream service, generates a second audit concerning a resource owned by the downstream service and having the trace ID, second span ID, and parent span ID as metadata, and persists the second audit to a second database. The audit service receives and asynchronously centralizes the first and second audits. The metadata can be used to infer causality of the audits. A method for preserving causality of audits is also disclosed and claimed.

11 Claims, 7 Drawing Sheets

(51) Int. Cl.
*G06F 21/62* (2013.01)
*H04L 29/06* (2006.01)
*G06F 16/27* (2019.01)
*G16H 10/20* (2018.01)

(52) U.S. Cl.
CPC ......... *G06F 21/6218* (2013.01); *G16H 10/20* (2018.01); *H04L 63/08* (2013.01)

(56) References Cited

U.S. PATENT DOCUMENTS

| | | | | |
|---|---|---|---|---|
| 2006/0293924 | A1* | 12/2006 | Gardiner | G06Q 50/24 705/3 |
| 2007/0213602 | A1* | 9/2007 | Ketcherside, Jr. | G16H 50/20 600/300 |
| 2009/0080408 | A1* | 3/2009 | Natoli | H04L 45/00 370/351 |
| 2009/0276463 | A1* | 11/2009 | Miller | G06F 19/3418 |
| 2009/0319535 | A1* | 12/2009 | Webber | G06F 16/252 |
| 2011/0145593 | A1* | 6/2011 | Auradkar | G06F 21/6218 713/189 |

OTHER PUBLICATIONS

PTAB Decision on Appeal, Appeal No. 2017-002714, U.S. Appl. No. 14/053,405 (Oct. 31, 2018).

\* cited by examiner

| Audit ID | Time | From | To | Dependency | Data |
|---|---|---|---|---|---|
| 301 | 12202 | A | B | $a_1$ | Blood pressure 100/60 |
| 302 | 12210 | B | C | $d_1$ | Blood pressure 120/80 |
| 303 | 12212 | B | E | $b_1$ | Blood pressure low |
| 304 | 12240 | B | D | $a_2$ | Temperature 37 |
| 305 | 12223 | E | G | $b_2$ | Trial protocol |
| 306 | 12267 | E | H | $c_1$ | Heart rate 72 |
| 307 | 12251 | D | F | $a_3$ | Nurse |
| 308 | 12260 | E | I | $e_1$ | Machine name |

SYSTEM AND METHOD FOR PRESERVING CAUSALITY OF AUDITS

CROSS-REFERENCE TO RELATED APPLICATION

This application is a continuation-in-part of and claims priority from U.S. application Ser. No. 14/053,405, filed on Oct. 14, 2013, the entirety of which is hereby incorporated by reference.

BACKGROUND

Data may be recorded and/or generated by numerous data recording devices. Examples of such devices are computer systems used in clinical trials (e.g., electronic data capture (EDC), safety, or randomization systems), computer systems used by healthcare professionals (e.g., electronic health records (EHR) or electronic medical records (EMR) systems), computer systems used by consumers (e.g., electronic patient-reported outcomes (ePRO) systems), medical devices (e.g., a blood glucose device used in a home, or an ECG in a clinic), consumer devices (e.g., a blood pressure cuff used on a phone, or an activity tracker), and centralized systems for storage of data from devices (e.g., in the cases of activity trackers, which often send their data via the Internet to the "cloud"). Other devices capturing clinical data are used in pre-clinical and post-marketing studies as well.

Currently, these different clinical data recording devices may provide or export data in different formats or via specific types of interchange protocols or standards, such as HL7 (Health Level Seven), CDISC/ODM, and E2B. In the United States, HL7's messaging standard is supported by most major medical information systems vendors. CDISC standards, set by the standards developing organization (SDO) of the same name, are platform-independent data standards used in clinical research. Even with the use of communication standards, clinical data recording devices transmit (export) data or generate their own audit trails, which data may not be standardized and thus may not be usable in combination with that of other devices.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

Embodiments of the present invention may be used in a variety of applications. For example, the techniques disclosed herein may be used in clinical trials, collection of medical and activity data for use by healthcare providers or payers, or in other systems containing disparate data input functionalities. A specific example may be in the field of consumer electronic entertainment systems, wherein devices or components from disparate manufacturers having heterogeneous data format, type, functionality, and/or data or communication exchange protocols could advantageously operate as a homogeneous or unified system. Because they lack a universal standard by which they can communicate, the clinical data recording devices discussed herein may be unable to interact with each other as a homogeneous system. Moreover, disparate protocols or standards make it difficult to create a consistent, usable audit trail for use by regulators or to reconstruct clinical data in the event of a system(s) failure or for post-market use.

Embodiments of the present invention allow disparate (heterogeneous) clinical data recording devices (also called "clinical data input functionalities" or "data-exporting devices" in this application) to be assimilated into a unified clinical system that is able to function regardless of the disparate data protocols of the recording devices. One way of realizing this system is by "cascading" a consistent (e.g., a usable, though not necessarily uniform) set of "audits" generated from data received from clinical data recording devices through downstream clinical components or systems, which audits ultimately provide a permanent and indelible record, in keeping with the regulatory requirements that govern many clinical trial systems. In some embodiments, the cascaded audits may also serve as a means of communication or instruction between the different components (clinical data recording devices or other downstream clinical systems) of a unified clinical system. Examples of clinical data recording devices are EDC systems, randomization systems, coding systems, health or activity tracking devices (called "activity trackers" herein) such as Nike+ FuelBand®, Jawbone Up™, Withings Pulse™, or Fitbit Flex™, and ECG and glucose monitors. Embodiments of the present invention may also provide that the transactions from such functionalities are fault-tolerant and reconstructable in the event of damage or data loss to components of the system, or for later reconstruction of the system, e.g., years after completion of a trial conducted with the system.

Figure 1A:
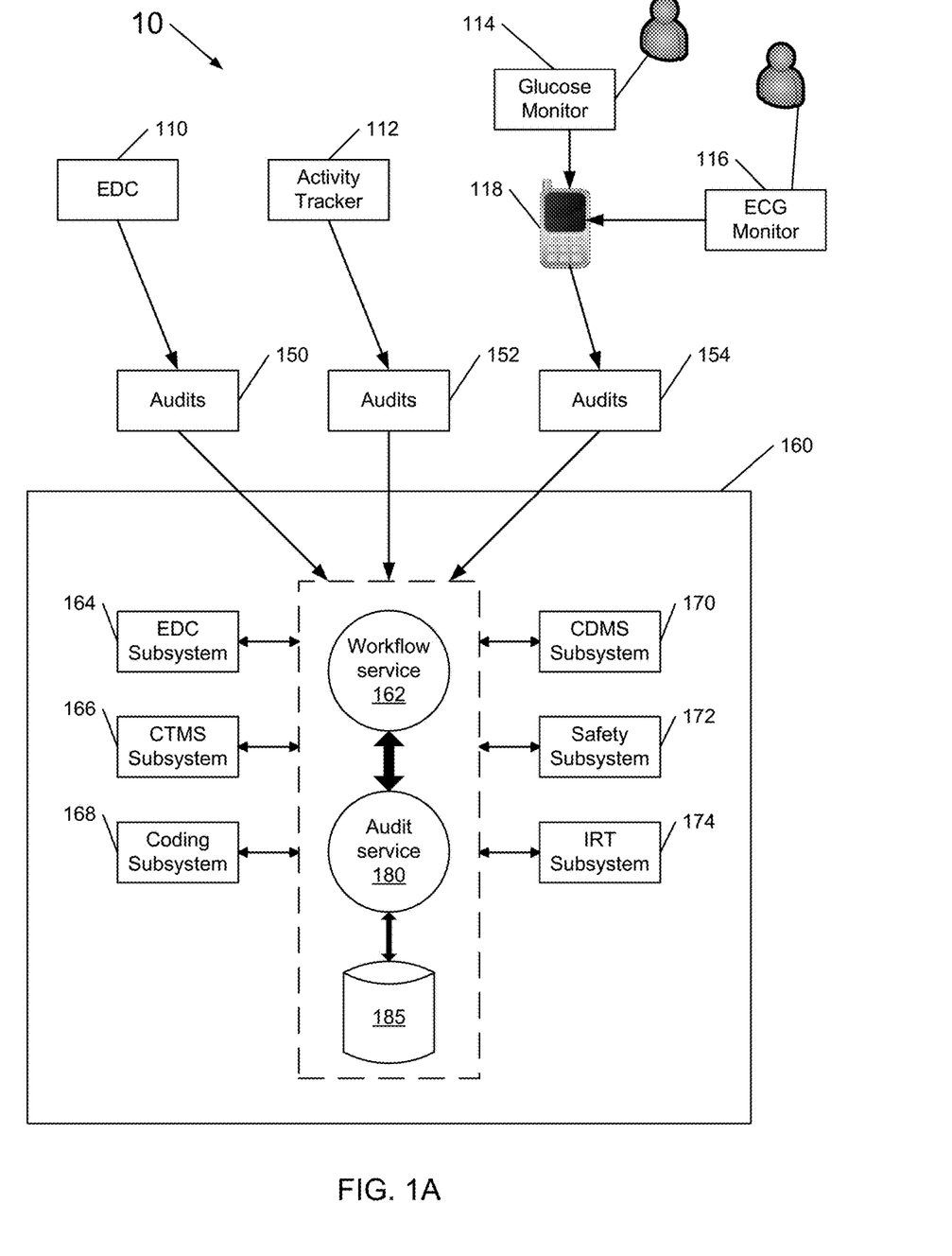
FIGS. 1A-1C are block diagrams of a system for collecting audits or data from various clinical data input functionalities according to several embodiments of the present invention.

Reference is now made to FIG. 1A, which is a block diagram of a system 10 for generating, collecting, processing, utilizing, and/or cascading audits derived from the data exported (export data) by various clinical data input functionalities. Audits or export data from the clinical data input functionalities are input to clinical data system 160, which system utilizes or processes the audits and/or transmits them to audit service 180 connected to an audit database 185, which may be a standalone or distributed datastore, such as Apache Cassandra.

As used in this specification, an audit is a record of a transaction occurring at one or more of the clinical data input functionalities or any downstream clinical system or component of clinical data system 160. An audit may include clinical data, operational data, or both, generated as a result of the transaction executed at a clinical data input functionality or a downstream component. Such clinical data may include height, weight, blood tests, blood pressure, activity metrics, glucose levels, ECG data, and other pharmacokinetic and pharmacovigilance data. Such operational data may include time stamps, vector clocks, and, more broadly, causality-determining markers associated with the executed transaction. Such operational data may also include data regarding what action was taken, who took the action, the identity of a device used to take the action (e.g., record some data), on whose behalf the action was taken, when the action was taken, what was changed from a previous state, the reason for the change, and what other audits may be related to it (e.g., identified by transaction ID), along with other information. (An "action" as used herein may include recording, calculating, converting or transmitting data, and may be a subset of or coextensive with a transaction.)

Figure 6:
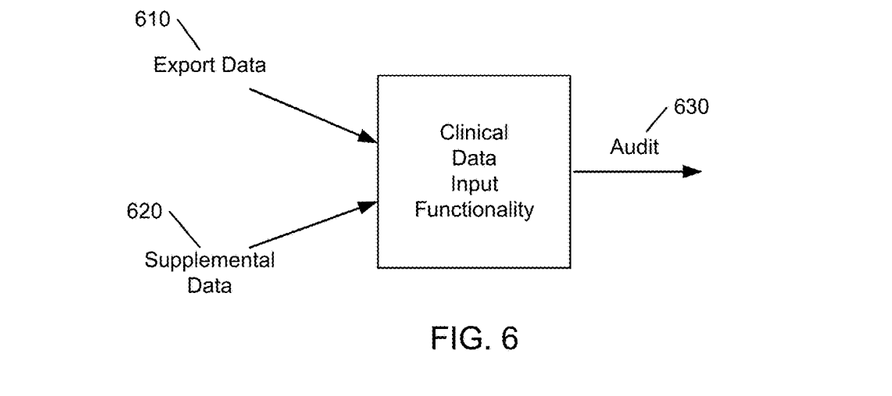
FIG. 6 is a block diagram showing the generation of an audit, according to an embodiment of the present invention.

As will be described further herein, an audit of the present invention may simply be constituted by the data received from a clinical data input functionality. However, where such received data is insufficient to constitute an audit of clinical data system 160, it may be supplemented by another audit, which audit may be generated in relation to the received data at a component of data system 160 (which may sometimes be workflow service 162) as necessary to constitute a sufficient audit. (The sufficiency of an audit, described with reference to the clinical data embodiments herein, may be a variable, configurable attribute of clinical data system 160.) Most simply, as shown in FIG. 6, where the export data 610 is insufficient to constitute an audit, supplemental data 620 may be captured in a subsequent audit by workflow service 162, which supplemental data 620 in combination with export data 610 may generate a sufficient audit 630.

Moreover, in contrast to the use of audits in the prior art, which were recorded in a database specific to individual clinical devices or systems, the use of audits of the present invention includes the cascading of audits for persistence and collection at a common or central audit service and audit database, as described further herein. Related, an "audit group," as used in this specification, is a group of audits linked by one or more dependencies (further described herein with reference to FIGS. 4 and 5).

Shown in FIG. 1A are several clinical data input functionalities, including EDC 110, activity tracker 112, and other clinical data sources, such as glucose monitor 114 or ECG monitor 116, which may generate and provide export data or audits directly or may interface with a device such as smartphone 118 through which they provide their export data or audits. Audits 150, 152, 154 may be the data exported by each clinical data input functionality (export data) or they may be data exported by such devices as audits, and clinical data system 160 may receive such audits; in either case, received audits may be insufficient for purposes of clinical data system 160 and may be supplemented as described further herein. Clinical data system 160 is shown in FIG. 1A as being made up of multiple downstream components, including workflow service 162, EDC subsystem 164, CTMS (clinical trial management system) subsystem 166, medical coding subsystem 168, CDMS (clinical data management system) subsystem 170, safety subsystem 172, and IRT (interactive response technology) subsystem 174. Downstream components within clinical data system 160 may or may not differ from each other with regard to data exchange or formatting standards, and may or may not be interoperable. For example, EDC subsystem 164 may differ from EDC 110 in that the latter, if not provided by the same manufacturer or distributor, may utilize different data formatting standards, such as data type extensions, or field naming conventions, such as the name for a time stamp or clinical measure. In other embodiments, however, clinical data input functionalities 110-118 may utilize the same data formatting or field naming standards as those used within clinical data system 160. (An EDC system, as used herein, may include internet-based clinical data capture software having validation components to verify entered data.)

Workflow service 162 may provide workflow instructions by which the export data and/or audits it receives are transmitted to the downstream components of clinical data system 160. For example, workflow service 162 may receive audits 150, 152, 154 from clinical data input functionalities 110-118, parse the received audits and, based on the stored workflow instructions and the audit data, calculate specific workflow instructions regarding where to transmit or route audits 150, 152, 154, e.g., to EDC subsystem 164 or directly to other downstream components. After receipt, EDC subsystem 164 may recursively transmit received audits 150, 152, 154 back to workflow service 162, which in turn may calculate further workflow instructions and transmit the audits to EDC subsystem 164 or to other downstream clinical components, such as CTMS subsystem 166, medical coding subsystem 168, CDMS subsystem 170, safety subsystem 172, and/or IRT subsystem 174 (either in sequence or in parallel).

In the just-described embodiments, wherein workflow service 162 may be viewed as functioning in a hub-and-spoke-type relationship with downstream components, workflow service 162 may also transmit audits 150, 152, 154 to audit service 180, in sequence or in parallel to their transmission to the downstream components. Thus the audits received by workflow service 162 (either initially from clinical devices 110-116 or recursively from downstream components 166-174) may function as a copy or copies of audits received and persisted by audit service 180. The transmission of audits to audit service 180 and to downstream components may be accomplished by parsing the data of the audits and passing that data as parameters via remote procedure call (RPC) to audit service 180 or to downstream components 166-174.

Figure 1B:
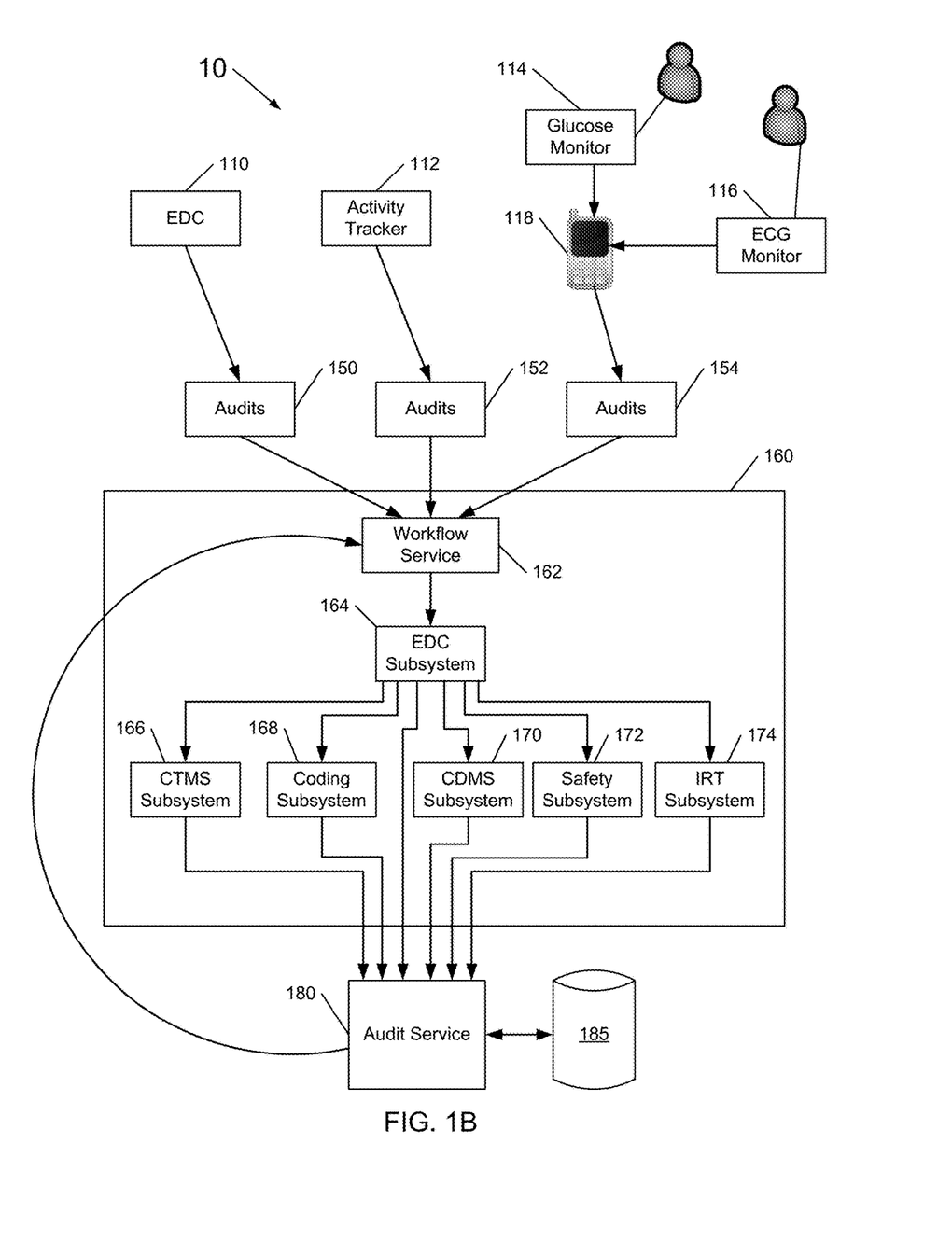
Figure 1C:
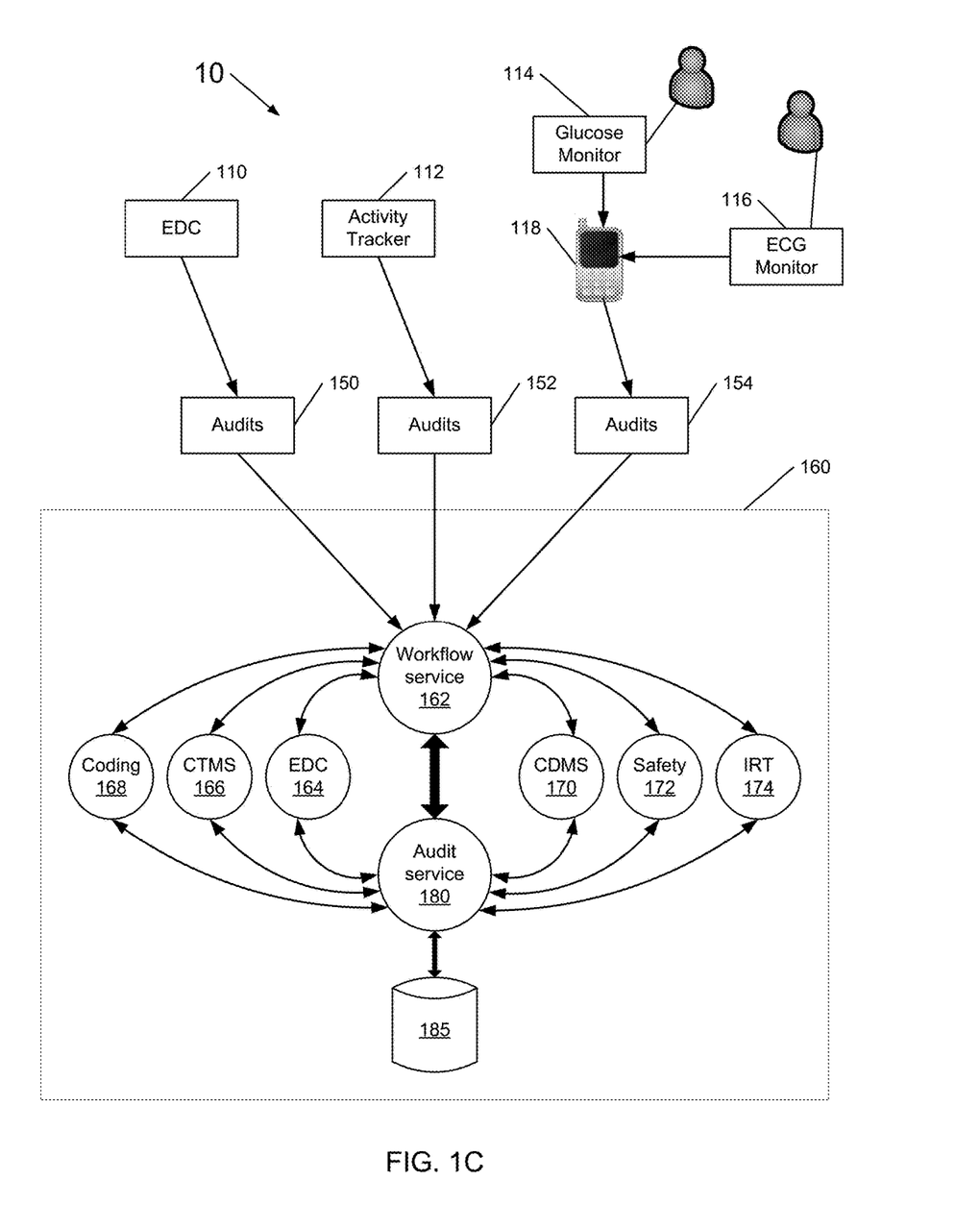

In alternative embodiments, shown in FIG. 1B, workflow service 162 may be configured to transmit audits (or audit groups) directly to more than one downstream clinical component 166-174, i.e., without requiring transmission of the audits back to workflow service 162 (on the basis of the workflow instructions or on the basis of component-based calculations, as described further herein). For example, workflow service 162 may bind workflow instructions to a received audit 150 by which that audit may be transmitted to EDC subsystem 164, then to safety subsystem 172, then to IRT subsystem 174, and finally to audit service 180, without being returned to workflow service 162 for further parsing and instruction. Alternatively, such embodiments may include transmission of audits 150, 152, 154 from workflow service 162 directly to one or more other clinical system components 166-174, bypassing EDC subsystem 164, as shown in FIG. 1C. As with the embodiments described with reference to FIG. 1A, workflow service 162 in FIGS. 1B and 1C may also transmit audits 150, 152, 154 to audit service 180, in sequence or in parallel to their transmission to the downstream components 166-174. As may be appreciated by one of skill in the art, other embodiments of the elements of the present invention may be configured.

After being received by one or more components or subsystems of clinical system 160, audits 150, 152, 154 may then be transmitted to audit service 180, which may persist audits to audit database 185 and/or recursively forward them to workflow service 162. The logic determining when audits (or any audits in an audit group) no longer recursively are directed back to workflow service 162 (called a "stopping point") may be determined by the instructions of the workflow service itself, or by component-based calculations based on received audits, and may occur when there is no more workflow to execute. Further, where it is utilized in place of a disparate EDC 110, EDC subsystem 164 may operate as a clinical data input functionality, transmitting audits to workflow service 162, to other downstream clinical system components, or to audit service 180.

Persisting and collecting audits and audit groups in a single audit service and database is valuable because it allows for the creation of a single, integrated, permanent and indelible audit trail for an entire clinical system, inclusive of disparate, heterogeneous clinical data input functionalities. Such an integrated audit trail then may generate reliable clinical data, useful for quality control, regulatory compliance, and the ability to generate useful operational metrics from a single, trustworthy source. Those metrics may include those previously not obtainable in the art, including metrics concerning the frequency and speed of different kinds of transactions (e.g., how often data are changed, how quickly data are cleaned or verified, etc.).

In more detail, an audit may be bound to a workflow determined by workflow service 162. The workflow, i.e., workflow instructions, may be generated or calculated by a decentralized work-flow engine, such as hypermedia (a graph of links describing available transactions) to drive a distributed workflow for cascading audits (creating an audit group) as described herein. The workflow instructions, which may be stored on a database (not shown) accessible to workflow service 162, may direct a receiving component to operate on data received as part of audits 150, 152, 154, and may direct where, if anywhere, an audit is to be subsequently transmitted. As described herein, in some embodiments of the present invention, an audit may also be directed to audit service 180 and audit database 185 in parallel to being received by a subsequent clinical system component. The workflow service 162 itself may be configurable, and workflow instructions may be dynamically and flexibly implemented.

Moreover, in contrast to prior audit-generating systems, the audits of the present invention no longer function only as by-products of clinical transactions occurring at clinical data input functionalities and/or clinical system components, stored in local audit databases specific to those clinical data input functionalities or clinical system components. Rather, the audits of the present invention may also be communicated—and may themselves serve as instructions—between disparate clinical data input functionalities and/or other downstream components. Audits serving as instructions—in contrast to the workflow instructions of workflow service 162—may function as data-driven or event-driven programming, by which a receiving component (the above-mentioned component-based calculations) may calculate subsequent actions based on the received audit. As with the workflow instructions of workflow service 162, the calculated actions may direct a receiving component to operate on data received as part of audits 150, 152, 154, and may direct where, if anywhere, an audit is to be subsequently transmitted. Component-based calculations allow a receiving component more flexibility and independence in processing, e.g., the ability to dynamically calculate subsequent actions based on parsing the data contained in a received audit rather than based on workflow instructions from workflow service 162. Further, such components would not be required to create or provide new application programming interfaces (APIs) in order to communicate with other components of clinical data system 160. Audits serving as instructions to downstream components may be synchronous or asynchronous, or in parallel or serial, with receipt and recordation of audits by audit service 180.

The audits of the present invention, which may be received from clinical data input functionalities and/or generated by component-based calculations (e.g., as part of an audit cascade by workflow service 162 and/or any components of clinical data system 160), are capable of being utilized to reconstruct a clinical system, using techniques such as causality stamps, including vector clocks, Merkle trees, or other anti-entropy protocols or processes. In more detail, audits may consist of data concerning the originator of the clinical or operational data, the action taken by or with the data, the change or result of the action taken, the reason or purpose of the action, the context or machine (device ID) on which the action was taken, the relationship to other audits, if any, the audit's ordering (vector clock) relative to other audits, and clinical trial-specific contextual information, such as identifiers of a specific study, study arm, protocol, subject, and/or site. Using techniques described further below with reference to FIGS. 4 and 5, clinical data system 160 may time order, or interleave, the audits of an audit group whereby each individual service or component may add time or causality information to the audits it creates using, for example, a distributed algorithm. Audit service 180, or any other service or component, may subsequently utilize that causality information to order the audits. An audit 150, 152, 154 may also contain all information required to be compliant with, and to prove compliance with, clinical regulations, such as those contained in 21 CFR Part 11 governing electronic records, data privacy, or patient privacy regulations such as HIPAA. The sufficiency of data required to be an audit of the present invention (of clinical data system 160) may, like workflow instructions, be configurable. Such configuration, through workflow service 162, may include the scope of transactions or actions that are to be captured by audit service 180. For example, while all generated audits may be captured by audit service 180, mere workflow instructions to an audit (for example, sending an audit to a downstream clinical component) may not be captured by audit service 180. The scope of actions or transactions captured by audit service 180 corresponds to the sufficiency of an audit as configured for purposes of clinical data system 160.

In some embodiments of the present invention, the clinical data input functionalities, such as EDC 110 or activity tracker 112, may not transmit sufficient data to constitute an audit for use by clinical data system 160. Instead, the insufficient data, once received by a component of clinical data system 160, may be viewed as programmatically supplemented by one or more subsequent, dependent (described further with regard to FIGS. 4 and 5 herein) audits, which dependent audits contain data which is required to constitute an audit and which is correlatable to the insufficient, received data. Correlatable data may include identifiers of the protocol by which the clinical data in the audit are received, the clinical study, site(s), subject(s), and time, dependency or causality stamps. As a result, even clinical data input functionalities which inherently lack the capacity to generate a sufficient audit may advantageously be converted into audits of the present invention and thereby standardize any heterogeneous clinical data input functionalities 110, 112, 114, 116, and 118 with clinical data system 160. (Alternatively, clinical data input functionalities 110, 112, 114, 116, and 118 may transmit audits that are already standardized with clinical data system 160.)

Audits of the present invention may also be viewed as records of state machine transformations, by which a distributed system may be modeled and data loss may be prevented. Audits of the present invention may further be viewed as data- or event-driven programming, in which a receiving clinical system component may calculate actions to execute based on a received audit, or may further "supplement" a received audit (by cascading further audits, described herein) prior to transmitting it to a subsequent clinical system component, to workflow service 162, or to audit service 180. For example, as described further with reference to FIG. 5, a clinical system component may calculate whether a received audit contains data to be acted on and whether, and where, to transmit (cascade) the received audit. Clinical data input functionalities such as EDC 110, activity tracker 112, and smartphone-delivered clinical data sources, such as glucose monitor 114 or ECG monitor 116, may also provide a receipt, summarizing the clinical and operational data which they sent to a specific clinical subsystem 166-174 via workflow service 162. The specific clinical subsystem 166-174 or workflow service 162 may check the receipt to ensure that all clinical and operational data were indeed correctly and entirely received. Such checking may use causality stamps, including vector clocks, Merkle trees, or other anti-entropy protocols or processes.

The blocks shown in FIGS. 1A-1C are examples of modules that may comprise system 10 and clinical data system 160, and do not limit the blocks or modules that may be part of or connected to or associated with these systems. For example, there may be several workflow services 162 and some may not actually be part of clinical data system 160. Audit service 180 and audit database 185 are shown both as being part of clinical data system 160 and as not being part of system 160. There also may be other subsystems within clinical data system 160, and they may be differently related, but only six subsystems in one hierarchy are shown for ease of readability and comprehension. Some of these may be combined in various embodiments, such as EDC subsystem 164 and CDMS subsystem 170. The blocks in FIGS. 1A to 1C may generally be implemented in software or hardware or a combination of the two.

Figure 2:
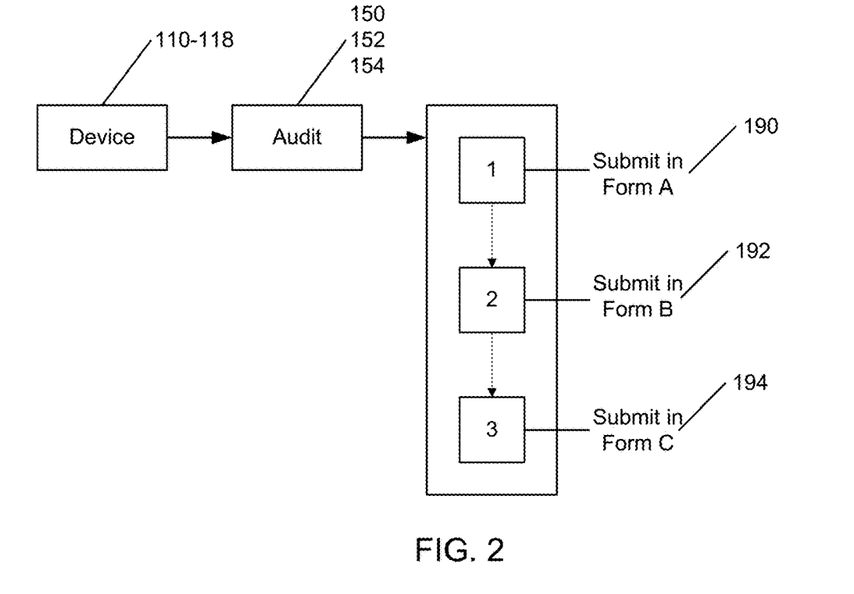
FIG. 2 is a block diagram of an audit containing data for submission into different electronic case report forms in an EDC system, according to an embodiment of the present invention.

Reference is now made to FIG. 2, which is a block diagram of an audit 150, 152, or 154 containing data 190, 192, 194 for submission into different electronic case report forms (eCRFs) or other clinical inputs A, B, C, respectively, in an EDC system. As the information enters clinical data system 160, workflow service 162 may provide instructions to EDC subsystem 164 as to which eCRF or eCRFs the audits and their data 190, 192 and 194 should be routed.

Figure 3:
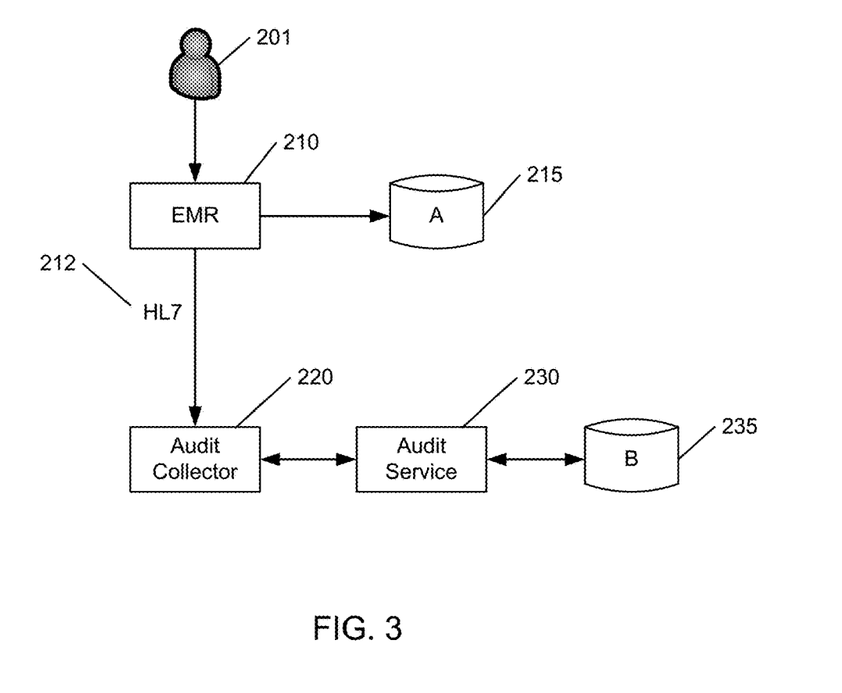
FIG. 3 is a block diagram of a system for collecting audits from an electronic medical records system, according to an embodiment of the present invention.

Reference is now made to FIG. 3, which is a block diagram of a system for collecting audits from an electronic medical records (EMR) system. The diagram is similar to FIGS. 1A-1C, but demonstrates what happens when the audit-producing system does not produce compatible audits. In this figure, a user 201, who, for example, may be a clinical trial patient, a nurse taking data from a patient, a principal investigator, or a clinical research associate (CRA), may enter data into EMR system 210. EMR system 210 normally produces audits and may store them in database A 215. In this figure, the EMR may also send audits in HL7 format 212 to audit collector 220, which is similar to clinical data system 160 in FIGS. 1A to 1C. Audit collector 220 may receive the audits from the EMR system and standardize them, as described above with reference to clinical data input functionalities that do not transmit all of the data required to constitute an audit of the present invention. The standardization process may allow audits to cascade to audit service 230 and include the raw data as well as the audit from EMR 210. These standardized audits may then be stored in database B 235. Clinical data system 160 and audit collector 220 as well as audit service 180, audit database 185, audit service 230, and database B 235 may be implemented on networks, for example, over the Internet as cloud-based services or hosted services, which may be accessed through standard web service APIs.

A benefit of standardizing the audits in this way has some regulatory compliance implications, as well. There are often questions about whether various EMR systems are "validated" to meet US FDA regulations such as 21 CFR Part 11 or similar regulations from international regulatory agencies. If all actions on clinical data (events) generate audits that may feed into the cascade and may become standardized, then the need to validate all the underlying code in EMR system 210 (or other clinical data input functionality 110-118) may be obviated.

Figure 4:
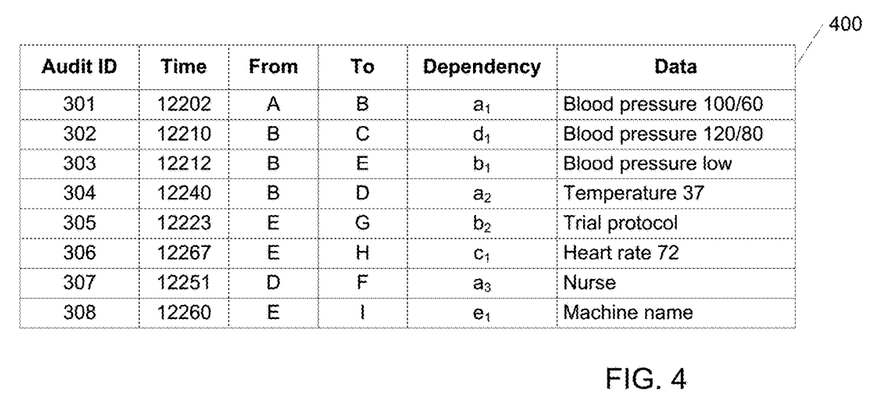
FIG. 4 is an audit log table having entries tracking the calls in FIG. 5, according to an embodiment of the present invention.

Reference is now made to FIG. 4, which is an audit log table. Audit log table 400 is an example of a table contained in audit service 180 or 230 useful for the tracking and re-creation of the flow of auditable transactions (events) such as those depicted and described further with reference to FIG. 5. Audit log tables may be useful in creating an audit trail to track and re-create events in a regulatory system, such as a clinical study. Users of the present invention, including clinical trial sponsors, contract research organization (CRO) personnel, or regulators, may want to track how data flows from one server to another or, more generally, from one node (clinical data input functionality or clinical system component) to another, especially in a distributed system in which the nodes have some independence from each other.

Figure 5:
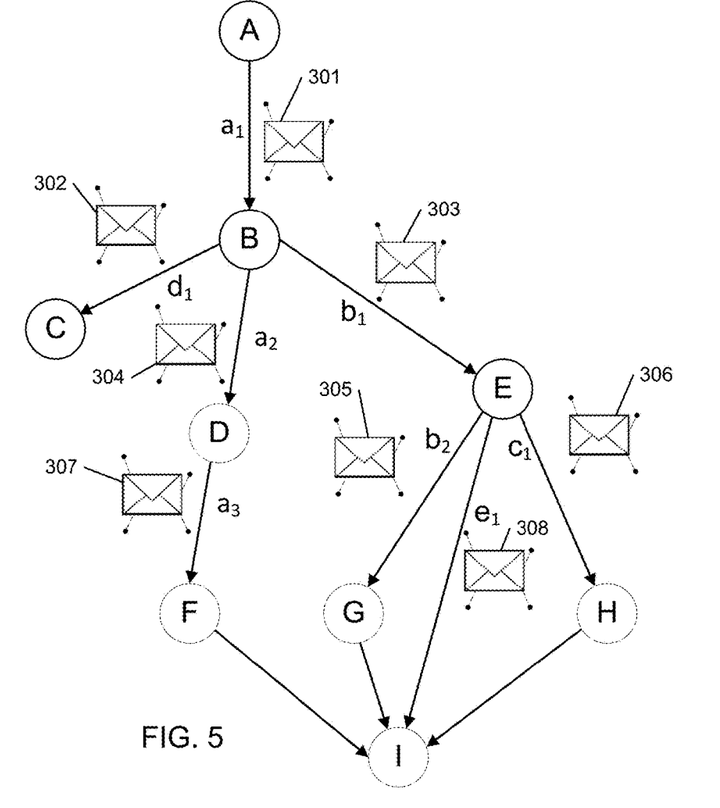
FIG. 5 is a diagram illustrating a call tree, according to an embodiment of the present invention.

According to an embodiment of the present invention, an audit log table may record the time at which audits 301-308 occurred, the nodes from and to which the audits are transmitted, the dependencies between the nodes within a given branch, and the clinical or operational data contained within the audits. In further detail, FIG. 5 is a schematic diagram of a "call tree" in a distributed system, which illustrates the paths of audits according to an embodiment of the present invention. The call tree is made up of nodes A through H, each of which may be servers, services, or software applications that operate on the audits, as well as node I, which may be audit service 180 or 230. Audits 301-308 are transmitted via nodes A through H as follows: audit 301 is transmitted from node A to node B; audit 302 is transmitted from node B to node C; audit 303 is transmitted from node B to node E; audit 304 is transmitted from node B to node D; audit 305 is transmitted from node E to node G; audit 306 is transmitted from node E to node H; audit 307 is transmitted from node D to node F, and audit 308 is transmitted from node E to node I. Each of these audits may generate an audit log table entry, which may include an Audit ID (e.g., 301-308), the transmission time, the originating node, the destination node, a dependency, and data contained within the audit.

When an audit is transmitted from a first node to a second node, either node may calculate (add or update, based, e.g., on a distributed algorithm) a dependency for recordation in the audit log table 400. For example, where audit 301 is sent from node A to node B, node A sets a first dependency, $a_1$. Where audit 304 is transmitted along the same branch to node D, a further dependency $a_2$ may be set by node B. Where audit 302 is transmitted along a different branch to node C, a new dependency $d_1$ may then be set. As these audits are cascaded from node to node, the new audits added or appended to earlier audit(s) through dependencies (existing audits do not get modified) generate an audit group, i.e., audits related by one or more dependencies. Audit groups are key to calculating or re-construct the causes of auditable transactions or events, and not just the sequence of those events. Further, dependencies allow the system to handle data that does not have a valid time stamp that comes from an external system.

As discussed previously, some embodiments of the present invention may use component-based calculations to calculate whether a received audit contains data on which that node should act, including to which subsequent node the received audit may be transmitted and whether the transmission should take place. As an example, node A may be viewed as activity tracker 112, node B as EDC subsystem 164, node E as safety subsystem 168, node Gas IRT subsystem 170, and node I as audit service 180. In that configuration, data such as a blood pressure (BP) reading may be generated at node A and received as part of audit 301 at node B, whereupon node B may calculate whether the received data is actionable by B. Node B may calculate that the received data is a BP reading and is actionable, and further may execute data cleaning/checking calculations (known as "queries") based upon the data. Those queries executed at node B may calculate that the received BP reading has a low value, indicating that that subject's BP is too low. Node B may then send a notification of low blood pressure to node E, a safety system, as part of audit 303, where node E may calculate, based on the received data, safety-related actions specific to the received BP value. Node E may then, simultaneously or sequentially, send audit 305 to node G, and audit 308 to node I, where node G may calculate, based on the received data, that a clinical trial arm must be rebalanced given that the subject with low BP may not be permitted to be enrolled in the clinical trial, and where node I may receive the previous audits 301, 303, 305, prior to or simultaneous to receiving audit 308.

In further detail, one of the columns in audit log table 400 is "time." This time may correspond to the time at the specific origination node or destination node or may be a more universal time (e.g., universal time "UTC"), such as may be derived from a common clock, possibly where the nodes use a GPS service linked to a common satellite or atomic clock. In some embodiments, it may not be necessary to record absolute time, rather it may just be sufficient to know relative time, i.e., which messages occurred before other messages. As discussed herein, for audits lacking correlatable time information, the audits generated by a first subsequent receiving node may calculate time information. Similarly, as time information may be lacking or linkage to a common clock may involve problematic delay, the use of a distributed algorithm to generate the dependencies of table 400 and the audit groups described herein may be appreciated.

As may be seen with reference to FIG. 4, the times at which an audit is received from or sent to a node may not be in order relative to recorded times for other audits within the call tree. For example, the time at which audit 304 passes from node B to node D is 12240, whereas the time at which audit 305 passes from node E to node G is earlier, 12223. Through the use of the dependencies recorded in the audit log table for audits 304 and 305, it is known that $b_1<b_2$, and that $a_1<a_2$, so while the transactions within the "a" transaction pair and the "b" transaction pair may be ordered, there may be no way to order transactions between the two pairs. The use of dependencies to order operations and identify concurrent operations in the present invention may also be significant to overcome clock drift, i.e., the differences in times recorded by the clocks local to different devices or components. With respect to the recreation of a flow of audits, it may be appreciated that where audit 301 contains the data "blood pressure 100/60" and audit 302 contains the data "blood pressure 120/80," and by virtue of dependency $d_1$ coming after $a_1$, then the operation of node B was to change the value of a piece of data from "blood pressure 100/60" to "blood pressure 120/80."

Figure 7:
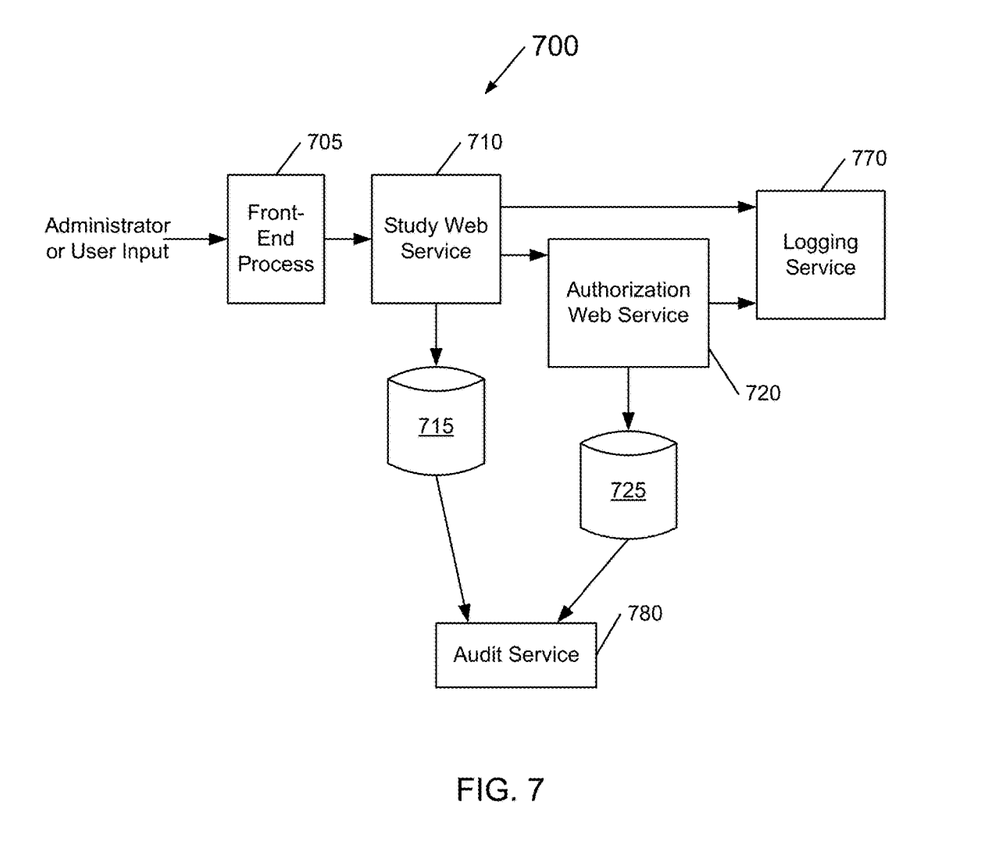
FIG. 7 is a block diagram of a system 700 having two services providing audits to an audit service and logging changes to a logging service, according to an embodiment of the present invention.
Figure 8:
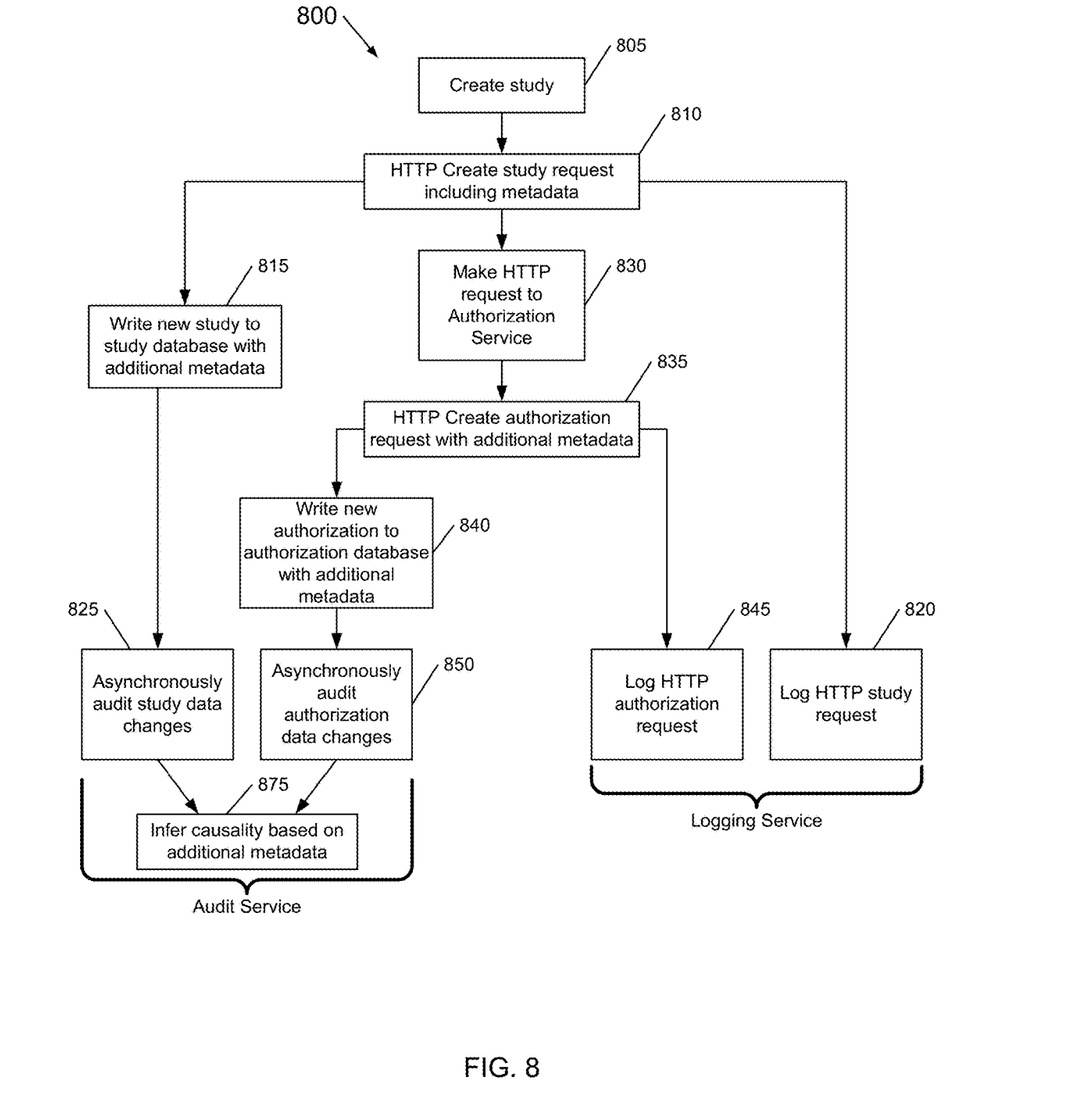
FIG. 8 is a flowchart showing the operations involved in the system shown in FIG. 7, according to an embodiment of the present invention.

Another way of determining a causal relationship among audits is shown in FIGS. 7 and 8. This technique uses existing, general logging protocols, but adds a number of steps and types of data that identify the causality for each audit. This technique is an improvement to the causality determining technology and improves the way such systems operate.

FIG. 7 is a block diagram of a system 700 having two services providing audits to an audit service and logging changes to a logging service. The two services may be an upstream service such as study web service 710 and a downstream service such as authorization web service 720. These services provide or persist audits to study database 715 and authorization database 725, respectively, which in turn provide or persist their audits to audit service 780, which operates in a manner similar to that of audit service 180 in FIGS. 1A-1C and audit service 230 in FIG. 3. System 700 may include front-end process 705, which may include a user interface, a website, an Excel file, or some other program that allows a human to write to study web service 710. Although not shown in FIG. 7, there also may be other interfaces between front-end process 705 and study web service 710.

System 700 may be used In the case of a clinical trial participant being assigned to a study such as a clinical trial. In such a situation, a clinical trial administrator may press a button to create a study, which may trigger front-end process 705 to generate a first HTTP request to study web service 710. Study web service 710 then logs the HTTP request to logging service 770, writes the new study to study database 715, and generates a second HTTP request to authorization web service 720 to inform that service that the administrator is the owner of that study. Authorization web service 720 may then log the second HTTP request to logging service 770 and write the new authorization to authorization database 725. Later, the two logs may asynchronously be put into the same store, e.g., logging service 770, and audits related to the two request records may asynchronously be put into a different store, e.g., audit service 780.

However, since the two request records may asynchronously be put into the same logging store, the causal relationship between those two log entries may not be apparent to someone looking at that store. Moreover, the causal relationship between the two audits may not be apparent to someone looking at the audit store.

For the log entries, embodiments of the present invention may use a combination of the Dapper project (from Google®) and the Zipkin project (from Twitter®). Dapper is a large-scale distributed systems tracing infrastructure; Zipkin is a distributed tracing system that gathers timing data for the disparate services involved in managing a request to the Twitter Application Programming Interface (API). Both projects are open source. Zipkin adds metadata to the first HTTP request that inform metadata in the second HTTP request, which are captured in the logs. The log information is then used to correlate the two records of the requests once they are in the logging service.

The inventors have modified Zipkin and Dapper by writing the metadata into both the log and audit stores (rather than just the log stores), which are associated with different records. The metadata are merged into the metadata for the audits. Using methods different from the logging function, the audits are correlated by inferring a causality tree from the associated metadata.

Reference is now made to FIG. 8, which is a flowchart 800 showing the operations involved in system 700. In operation 805, a clinical trial administrator may create a study and may assign herself to that study. In operation 810, an HTTP study request may be created, e.g., by front-end process 705, that includes metadata such as a trace ID and a span ID. Since this is the first HTTP request, the trace ID will be named "trace_ID_1" and the span ID will be named "span_ID_1." In operation 815, the new study may be written to study database 715. This study is saved with the additional metadata trace_ID_1 and span_ID_1 used for auditing. This operation generates a first audit concerning a resource (e.g., a study) owned by an upstream service (e.g., study web service 710) and having trace_ID_1 and span_ID_1 as metadata. In operation 820, a log HTTP study request may be made to logging service 770. In operation 825, study data changes may be asynchronously audited and persisted and centralized in audit service 780.

In operation 830, study web service 710 may make an HTTP request to authorization web service 720. In operation 835, an HTTP authorization request may be created that includes some of the same metadata as before, but also includes some different and additional metadata. The trace ID remains the same (trace_ID_1), but a new span ID is generated—"span_ID_2"—and span_ID_1 is converted and relabeled with another piece of metadata—parent span ID—which in this case may be named "parent_span_ID_1" to show that the audit came from span_ID_1. In operation 840, the new authorization may be written to authorization database 725. This authorization is saved with the additional metadata trace_ID_1, span_ID_2, and parent_span_ID_1 used for auditing. This operation generates a second audit concerning a resource (e.g., an authorization) owned by a downstream service (e.g., authorization web service 720) and having trace_ID_1, span_ID_2, and parent_span_ID_1 as metadata. In operation 845, a log HTTP authorization request may be made to logging service 770. In operation 850, authorization data changes may be asynchronously audited and persisted and centralized in audit service 780.

In operation 875, audit service 780 is able to infer causality based on the additional metadata in the requests. By comparing the trace_ID, span_ID, and parent_span_ID of the two audits, causality may be determined even if the second audit is stored in the audit service first (since storage is asynchronous). In this example, the study audit includes trace_ID_1 and span_ID_1, whereas the authorization audit includes trace_ID_1, span_ID_2, and parent_span_ID_1. Although both include the same trace ID, the span ID of the authorization audit is span_ID_2, which is known to have been put into the audit after span_ID_1. The authorization audit also includes parent_span_ID_1, which shows that its parent is span_ID_1, which is the span ID of the study audit. Thus, it can be determined that the study audit occurred before the authorization audit. As more audits are generated, a new span ID will be generated, and the old span ID will be converted and relabeled as a parent span ID. Cascading audits may thus be grouped by the trace ID, and causality may be determined from the parent span ID/span ID relationship.

Besides the operations shown in FIG. 8, other operations or series of operations are contemplated to resolve causality of audits. There may be more than two services, thus necessitating more requests, more audits, and more span IDs and parent span IDs. Moreover, the actual order of the operations in the flowchart is not intended to be limiting, and the operations may be performed in any practical order. For example, the logging and storing operations may be performed asynchronously. And the while the example calls the study web service an "upstream service" and the authorization web service a "downstream service," in a different workflow, the two services' relationship with each other may change, so that the study web service is downstream from the authorization web service. So, there could be more complicated paths, such as service A calling service B, service B calling service C, and service C calling services A, B, and D in parallel. In such a parallel example, if an operation OC in service C involves calls to services A, B, and D, causing operations OA, OB, and OD in those services respectively, the system would be able to correctly infer that causality existed between OC and OA, OC and OB, and OC and OD, and not between OA, OB, and OD.

This process for determining causality of audits differs from the Zipkin/Dapper logging protocol because audits are transactional, optimized for reliability over speed, and permanent, while logs are non-transactional, optimized for speed, and transient. This means that entirely separate systems are used to generate the audits, so duplicating metadata between one system and another is not trivial and not a simple solution. Moreover, generating audits concerning resources (e.g., the study or the authorization) owned by the upstream and downstream services and having the trace ID, span ID, and parent span ID as metadata differs from the logging protocol. In addition, persisting the study audit and the authorization audit to databases, before transmitting them to the audit service, also differs from the logging protocol.

The blocks shown in FIG. 7 are examples of modules that may comprise system 700 and do not limit the blocks or modules that may be part of or connected to or associated with this system. For example, although FIG. 7 shows front-end process 705 and study web service 710 as separate blocks, study web service 710 could perform the functions of front-end process 705. In addition, although the figure shows study web service 710 and authorization web service 720, these services are just two examples of services that may generate audits and log changes; system 700 may have more than two services, including a study optimization service, an eLearning service, a user details service, and a coding service, each of which has an associated database.

These other services may act as further downstream services that may generate further audits concerning resources owned by these further downstream services. These further services also generate further span IDs and parent span IDs. Moreover, even though audits generated in a clinical trial are used as an example, this causality resolution method does not have to be used in clinical trials.

A benefit of the present invention is in the way audits are used and standardized. Before, an audit was a snapshot in time of what was occurring at a particular clinical data input functionality or component. With this invention, audits may be bound to a workflow, and the workflow may be recreated as a series of events. This workflow may be used as part of a submission to a regulatory agency to evaluate safety and efficacy of a drug or device. A further benefit of the present invention is that audits that cascade down to a subsystem, such as coding subsystem 168, may allow that subsystem to calculate its next actions, whereas previously, coding subsystem 168 would receive instructions from another system, such as EDC subsystem 164.

Receipt of an audit, i.e., the transaction detail, by EDC subsystem 164 differs from receiving values and properties directly from a clinical data input functionality. For example, for source data verification (SDV) in previous systems, when a data point is marked as verified (e.g., in an EDC system), additional data such as who verified the data, when they verified it, etc., is also recorded. That additional data however may be captured as part of the audits of the present invention. Thus, instead of redundantly receiving those values and properties, the system of the present invention may receive the audit description of the values and properties that also contain the information described above.

Aspects of the present invention may be embodied in the form of a system, a computer program product, or a method. Similarly, aspects of the present invention may be embodied as hardware, software or a combination of both. Aspects of the present invention may be embodied as a computer program product saved on one or more computer-readable media in the form of computer-readable program code embodied thereon.

For example, the computer-readable medium may be a computer-readable signal medium or a computer-readable storage medium. A computer-readable storage medium may be, for example, an electronic, optical, magnetic, electromagnetic, infrared, or semiconductor system, apparatus, or device, or any combination thereof.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that may communicate, propagate, or transport a program for use by or in connection with an instruction execution system, apparatus, or device.

Computer program code in embodiments of the present invention may be written in any suitable programming language. The program code may execute on a single computer, or on a plurality of computers. The computer may include a processing unit in communication with a computer-usable medium, wherein the computer-usable medium contains a set of instructions, and wherein the processing unit is designed to carry out the set of instructions.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A unified clinical system for determining causality of audits, comprising:
 a clinical study web service that receives a first HTTP request including a trace ID and a first span ID, generates a first audit concerning a resource owned by said clinical study web service and having the trace ID and the first span ID as metadata, persists the first audit to a study database, and generates a second HTTP request including the trace ID, a parent span ID, and a second span ID;
 an authorization web service that receives the second HTTP request from the clinical study web service, generates a second audit concerning a resource owned by said authorization web service and having the trace ID, second span ID, and parent span ID as metadata, and persists the second audit to an authorization database; and
 an audit service for receiving and asynchronously centralizing the first and second audits, wherein the trace ID, first and second span IDs, and parent span ID are used to determine causality.

2. The system of claim 1, wherein the clinical study web service converts the first span ID to the parent span ID and generates the second span ID.

3. The system of claim 1, further comprising a logging service for logging the first and second HTTP requests.

4. The system of claim 1, wherein the resource owned by the clinical study web service is a clinical study.

5. The system of claim 1, wherein the resource owned by the authorization web service is an authorization.

6. The system of claim 1, further comprising a front-end process that generates the trace ID, first span ID, and first HTTP request.

7. The system of claim 1, further comprising a study optimization service that receives an HTTP request from the authorization web service, generates a third audit concerning a resource owned by said study optimization service and having the trace ID, a third span ID, and a second parent span ID as metadata, and persists the third audit to a study optimization database.

8. The system of claim 7, wherein the audit service receives and asynchronously centralizes the third audit.

9. The system of claim 1, further comprising a study optimization service that receives an HTTP request from the clinical study web service, generates a third audit concerning a resource owned by said study optimization service and having the trace ID, a third span ID, and the parent span ID as metadata, and persists the third audit to a study optimization database.

10. The system of claim 1, wherein the first audit is based on an audit exported from a clinical device.

11. The system of claim 1, wherein the first audit is based on an audit from a workflow service.

* * * * *